(12) United States Patent
Cronin

(10) Patent No.: US 12,193,810 B2
(45) Date of Patent: Jan. 14, 2025

(54) SYSTEM AND METHOD FOR PERFORMING SURGERY WITH REAL-TIME HEALTH PARAMETER MONITORING

(71) Applicant: Know Labs, Inc., Seattle, WA (US)

(72) Inventor: John Cronin, Williston, VT (US)

(73) Assignee: KNOW LABS, INC., Seattle, WA (US)

( * ) Notice: Subject to any disclaimer, the term of this patent is extended or adjusted under 35 U.S.C. 154(b) by 0 days.

(21) Appl. No.: 18/187,314

(22) Filed: Mar. 21, 2023

(65) Prior Publication Data
US 2024/0315605 A1    Sep. 26, 2024

(51) Int. Cl.
*A61B 5/145* (2006.01)
*A61B 5/00* (2006.01)
*A61B 5/0507* (2021.01)

(52) U.S. Cl.
CPC ........ *A61B 5/14532* (2013.01); *A61B 5/0507* (2013.01); *A61B 5/14542* (2013.01); *A61B 5/7203* (2013.01)

(58) Field of Classification Search
CPC .............. A61B 5/14532; A61B 5/0507; A61B 5/14542; A61B 5/7203
See application file for complete search history.

(56) References Cited

U.S. PATENT DOCUMENTS

| | | | |
|---|---|---|---|
| 4,202,000 | A | 5/1980 | Carballes |
| 8,223,021 | B2 | 7/2012 | Goodnow et al. |
| 8,882,670 | B2 | 11/2014 | Hancock |

(Continued)

FOREIGN PATENT DOCUMENTS

| | | |
|---|---|---|
| EP | 3146898 B1 | 11/2018 |
| EP | 3981329 A1 | 4/2022 |

(Continued)

OTHER PUBLICATIONS

Majewski J, Risler Z, Gupta K. Erroneous Causes of Point-of-Care Glucose Readings. Cureus. Mar. 19, 2023;15(3):e36356. doi: 10.7759/cureus.36356. PMID: 37082479; PMCID: PMC10112488. (Year: 2023).*

(Continued)

*Primary Examiner* — Andrey Shostak
(74) *Attorney, Agent, or Firm* — HSML P.C.

(57) ABSTRACT

Methods of using a system for real-time monitoring of blood glucose levels and other analyte levels to reduce the risk of surgical complications. The system includes an apparatus for generating radio frequency scanning data which includes a transmitter for transmitting radio waves below the skin surface of a person and a two-dimensional array of receive antennas for receiving the radio waves, including a portion of the transmitted radio waves that interact with a blood vessel of the person. The wave signal is compared to known standard waveforms, and similar waveforms are input into a machine learning algorithm to determine one or more health parameters of the person. The apparatus is used to collect glucose waveform data. A second apparatus is used to collect waveform data on another analyte. The glucose waveform is analyzed to determine the patient's blood glucose level. The system reports risks associated with the patient's glucose level.

15 Claims, 5 Drawing Sheets

(56) References Cited

U.S. PATENT DOCUMENTS

Figure 1:
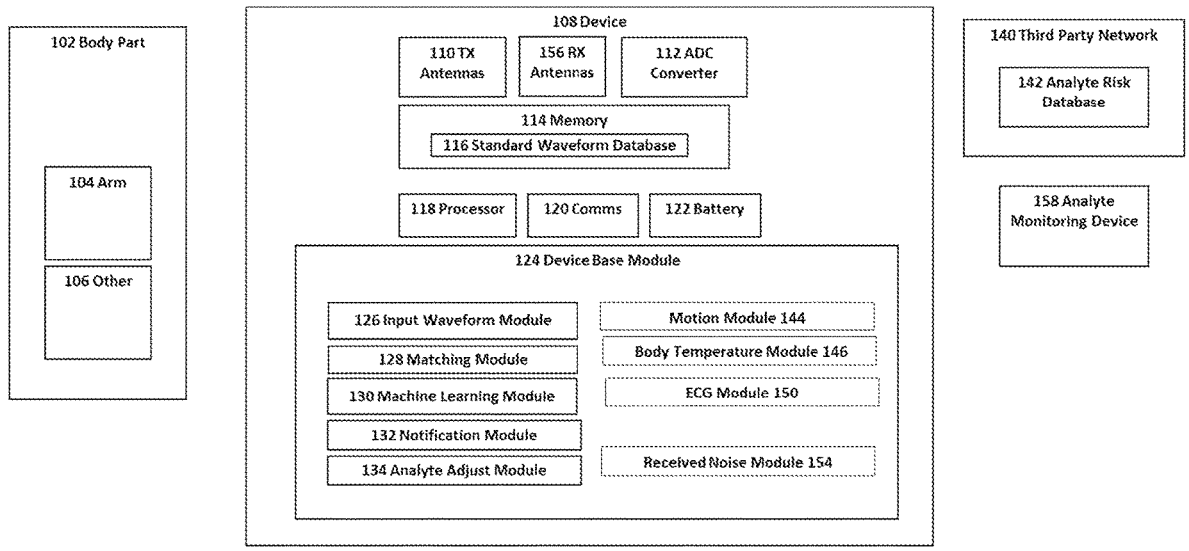

| | | |
|---|---|---|
| 9,198,607 B2 | 12/2015 | Fischer |
| 9,864,024 B2 | 1/2018 | Vester |
| 10,149,629 B2 | 12/2018 | Szczepaniak et al. |
| 10,478,101 B1 | 11/2019 | Cespedes et al. |
| 10,548,503 B2 | 2/2020 | Bosua |
| 10,617,296 B2 | 4/2020 | Sloan et al. |
| 10,856,766 B2 | 12/2020 | Leabman |
| 10,912,500 B2 | 2/2021 | Poeze et al. |
| 10,956,950 B2 | 3/2021 | Al-Ali et al. |
| 11,031,970 B1 | 6/2021 | Bosua |
| 11,033,208 B1 | 6/2021 | Bosua |
| 11,058,317 B1 | 7/2021 | Bosua |
| 11,058,331 B1 | 7/2021 | Bosua |
| 11,063,373 B1 | 7/2021 | Bosua |
| 11,193,923 B2 | 12/2021 | Bosua |
| 11,202,582 B2 | 12/2021 | Verkruijsse et al. |
| 11,223,383 B1 | 1/2022 | Bosua |
| 11,234,618 B1 | 2/2022 | Bosua et al. |
| 11,234,619 B2 | 2/2022 | Bosua |
| 11,244,753 B2 | 2/2022 | Haggerty et al. |
| 11,284,819 B1 | 3/2022 | Bosua et al. |
| 11,284,820 B1 | 3/2022 | Bosua et al. |
| 11,291,374 B2 | 4/2022 | Lee et al. |
| 11,298,037 B2 | 4/2022 | Leabman |
| 11,350,830 B2 | 6/2022 | McKenna et al. |
| 11,360,188 B2 | 6/2022 | Leabman |
| 11,367,525 B2 | 6/2022 | Addison et al. |
| 11,389,091 B2 | 7/2022 | Bosua |
| 11,389,093 B2 | 7/2022 | Triman et al. |
| 11,426,104 B2 | 8/2022 | Schurman et al. |
| 2003/0036713 A1 | 2/2003 | Bouton et al. |
| 2003/0235817 A1 | 12/2003 | Bartkowiak et al. |
| 2004/0065158 A1 | 4/2004 | Schrepfer et al. |
| 2004/0127777 A1 | 7/2004 | Ruchti et al. |
| 2004/0133086 A1 | 7/2004 | Ciurczak et al. |
| 2006/0001551 A1 | 1/2006 | Kraft et al. |
| 2008/0083617 A1 | 4/2008 | Simpson et al. |
| 2008/0214918 A1 | 9/2008 | Brister et al. |
| 2009/0099436 A1 | 4/2009 | Brister et al. |
| 2009/0137887 A1 | 5/2009 | Shariati et al. |
| 2009/0275814 A1 | 11/2009 | Watanabe et al. |
| 2009/0322513 A1 | 12/2009 | Hwang et al. |
| 2010/0041969 A1 | 2/2010 | Beise |
| 2011/0028814 A1 | 2/2011 | Petersen et al. |
| 2013/0096396 A1 | 4/2013 | Riedel |
| 2013/0184599 A1 | 7/2013 | Friedman et al. |
| 2014/0213870 A1 | 7/2014 | Hsu et al. |
| 2015/0257698 A1 | 9/2015 | Spratt et al. |
| 2016/0051171 A1 | 2/2016 | Pikov et al. |
| 2016/0157733 A1 | 6/2016 | Gil |
| 2016/0309535 A1 | 10/2016 | Myoung et al. |
| 2016/0361002 A1 | 12/2016 | Palikaras et al. |
| 2017/0095667 A1 | 4/2017 | Yakovlev et al. |
| 2018/0028824 A1 | 2/2018 | Pivonka et al. |
| 2018/0035901 A1* | 2/2018 | Cronin ............... A61B 5/00 |
| 2018/0132766 A1 | 5/2018 | Lee et al. |
| 2018/0242920 A1 | 8/2018 | Hresko et al. |
| 2019/0008422 A1 | 1/2019 | Leath et al. |
| 2019/0053741 A1 | 2/2019 | Chaudhry |
| 2019/0104939 A1 | 4/2019 | Costantine et al. |
| 2019/0269853 A1 | 9/2019 | Doyle et al. |
| 2019/0374135 A1 | 12/2019 | Poeze et al. |
| 2019/0388000 A1 | 12/2019 | Costantine et al. |
| 2020/0054255 A1 | 2/2020 | Conrad et al. |
| 2020/0057163 A1 | 2/2020 | Bromberg |
| 2020/0113485 A1 | 4/2020 | Wybo et al. |
| 2020/0146584 A1 | 5/2020 | Bosua |
| 2020/0187791 A1 | 6/2020 | Leabman |
| 2020/0187792 A1 | 6/2020 | Leabman |
| 2020/0187793 A1 | 6/2020 | Leabman |
| 2020/0187812 A1 | 6/2020 | Leabman |
| 2020/0187813 A1 | 6/2020 | Leabman |
| 2020/0187814 A1 | 6/2020 | Leabman |
| 2020/0187815 A1 | 6/2020 | Leabman |
| 2020/0187816 A1 | 6/2020 | Leabman |
| 2020/0187817 A1 | 6/2020 | Leabman |
| 2020/0187818 A1 | 6/2020 | Leabman |
| 2020/0187819 A1 | 6/2020 | Leabman |
| 2020/0187820 A1 | 6/2020 | Leabman |
| 2020/0187836 A1 | 6/2020 | Leabman |
| 2020/0187837 A1 | 6/2020 | Leabman |
| 2020/0187867 A1 | 6/2020 | Leabman |
| 2020/0191909 A1 | 6/2020 | Leabman |
| 2020/0191932 A1 | 6/2020 | Leabman |
| 2020/0191933 A1 | 6/2020 | Leabman |
| 2020/0191944 A1 | 6/2020 | Leabman |
| 2020/0191945 A1 | 6/2020 | Leabman |
| 2020/0191947 A1 | 6/2020 | Leabman |
| 2020/0192426 A1 | 6/2020 | Leabman |
| 2020/0192427 A1 | 6/2020 | Leabman |
| 2020/0192428 A1 | 6/2020 | Leabman |
| 2020/0193326 A1 | 6/2020 | Leabman |
| 2020/0195197 A1 | 6/2020 | Leabman |
| 2020/0195293 A1 | 6/2020 | Leabman |
| 2021/0134431 A1 | 5/2021 | Garcia et al. |
| 2021/0137468 A1 | 5/2021 | Katragadda et al. |
| 2021/0186357 A1 | 6/2021 | Bosua et al. |
| 2021/0194531 A1 | 6/2021 | Bosua |
| 2021/0219925 A1 | 7/2021 | Au et al. |
| 2021/0259571 A1 | 8/2021 | Bosua |
| 2021/0259592 A1 | 8/2021 | Bosua |
| 2021/0259593 A1 | 8/2021 | Bosua |
| 2021/0350896 A1 | 11/2021 | Shelton, IV et al. |
| 2022/0015695 A1 | 1/2022 | Margarito et al. |
| 2022/0031254 A1 | 2/2022 | Al-Ali et al. |
| 2022/0071527 A1 | 3/2022 | Bosua |
| 2022/0074870 A1 | 3/2022 | Bosua |
| 2022/0077918 A1 | 3/2022 | Bosua et al. |
| 2022/0108805 A1 | 4/2022 | Lee |
| 2022/0151553 A1 | 5/2022 | Bosua |
| 2022/0192494 A1 | 6/2022 | Leabman |
| 2022/0192522 A1 | 6/2022 | Leabman |
| 2022/0192531 A1 | 6/2022 | Leabman |
| 2022/0233119 A1 | 7/2022 | Shelton, IV et al. |
| 2022/0233241 A1* | 7/2022 | Shelton, IV ........... A61B 34/10 |
| 2022/0238216 A1 | 7/2022 | Shelton, IV et al. |
| 2022/0248965 A1 | 8/2022 | O'Brien et al. |
| 2022/0248984 A1 | 8/2022 | Poeze et al. |
| 2022/0257199 A1 | 8/2022 | Breton et al. |
| 2022/0287649 A1 | 9/2022 | Leabman |
| 2022/0322976 A1* | 10/2022 | Edla ................. A61B 5/725 |
| 2023/0263439 A1 | 8/2023 | Cheng et al. |
| 2024/0062870 A1 | 2/2024 | Rosenberg et al. |

FOREIGN PATENT DOCUMENTS

| | | |
|---|---|---|
| JP | 2012125382 | 7/2012 |
| JP | 2014147637 | 8/2014 |
| KR | 1020130142016 A | 12/2013 |
| KR | 1020160081740 | 7/2016 |
| KR | 1020220052078 A | 4/2022 |
| WO | 2009/082286 | 7/2009 |
| WO | 2017163245 | 9/2017 |
| WO | 2018/111690 | 6/2018 |
| WO | 2019071138 | 4/2019 |
| WO | 2019/178524 | 9/2019 |
| WO | 2019182638 | 9/2019 |
| WO | 2019217461 | 11/2019 |
| WO | 2020006077 | 1/2020 |
| WO | 2020037171 | 2/2020 |
| WO | 2021198045 A1 | 10/2021 |
| WO | 2022026623 A1 | 2/2022 |
| WO | 2022/157706 | 7/2022 |
| WO | 2023/028367 | 3/2023 |

OTHER PUBLICATIONS

C, Alex. "Heart Rate Is Here." Heart Rate Is Here, Mar. 14, 2023, www.veri.co/learn/heart-rate-data-veri. (Year: 2023).*

Dunbar, Brian. "What Are Radio Waves?" NASA, Aug. 31, 2018, www.nasa.gov/directorates/heo/scan/communications/outreach/funfacts/what_are_radio_waves. (Year: 2018).*

(56) References Cited

OTHER PUBLICATIONS

Nøstbakken, Roar Tordahl. "Cancellation of Movement Artifacts in Glucosesensor Data." NTNU Open, NTNU, Jun. 5, 2017, ntnuopen.ntnu.no/ntnu-xmlui/handle/11250/2457154. Accessed Jan. 13, 2024. (Year: 2017).*

Hanna, J. et al., "Noninvasive, wearable, and tunable electromagnetic multisensing system for continuous glucose monitoring, mimicking vasculature anatomy," Science Advances, 6, eaba5320, 2020 (11 pages).

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

Qiang et al., "Quantitative detection of glucose level based on radiofrequency patch biosensor combined with volume-fixed structures," Biosensors and Bioelectronics 98:357-363, 2017.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

Stojanovic, R. et al., "An optical sensing approach based on light emitting diodes," Journal of Physics: Conference Series 76 (2007), pp. 1-6.

Rossiter, J. et al., "A novel tactile sensor using a matrix of LEDs operating in both photoemitter and photodetector modes," Proc of 4th IEEE International Conference on Sensors (IEEE Sensors 2005), pp. 994-997.

Surgery Definition & Meaning, Aug. 22, 2023, Merriam Webster Dictionary (Year: 2023) https://www.merriam-webster.com/dictionary/surgery#:~:text=sur%C2%B7%E2%80%8Bgery%20%CB%88s%C9%99rj%2Dr%C4%93,to%20operative%20or%20manual%20procedures.

International Search Report and Written Opinion issued for International Patent Application No. PCT/US2024/020730, Date of mailing: Jul. 8, 2024, 8 pages.

* cited by examiner

SYSTEM AND METHOD FOR PERFORMING SURGERY WITH REAL-TIME HEALTH PARAMETER MONITORING

FIELD OF THE DISCLOSURE

The present disclosure is generally related to systems and methods of monitoring health parameters and, more particularly, relates to a system and a method of monitoring real-time glucose levels using radio frequency signals.

BACKGROUND

Blood glucose levels can change rapidly in patients undergoing surgery, especially those with conditions that affect blood glucose levels, such as diabetes.

Variations in blood glucose during a surgical procedure can result in delayed healing, increased wound infection, kidney issues, heart and/or lung problems, neurological complications, stroke, or even death.

It is difficult to measure blood glucose in real-time as current methods sample blood, and measurements could produce gaps and, therefore, inaccuracy of invasive testing or the requirement to continuously test blood samples.

DESCRIPTIONS OF THE DRAWINGS

FIG. 1: Illustrates a radio frequency health monitoring system, according to an embodiment.

Figure 2:
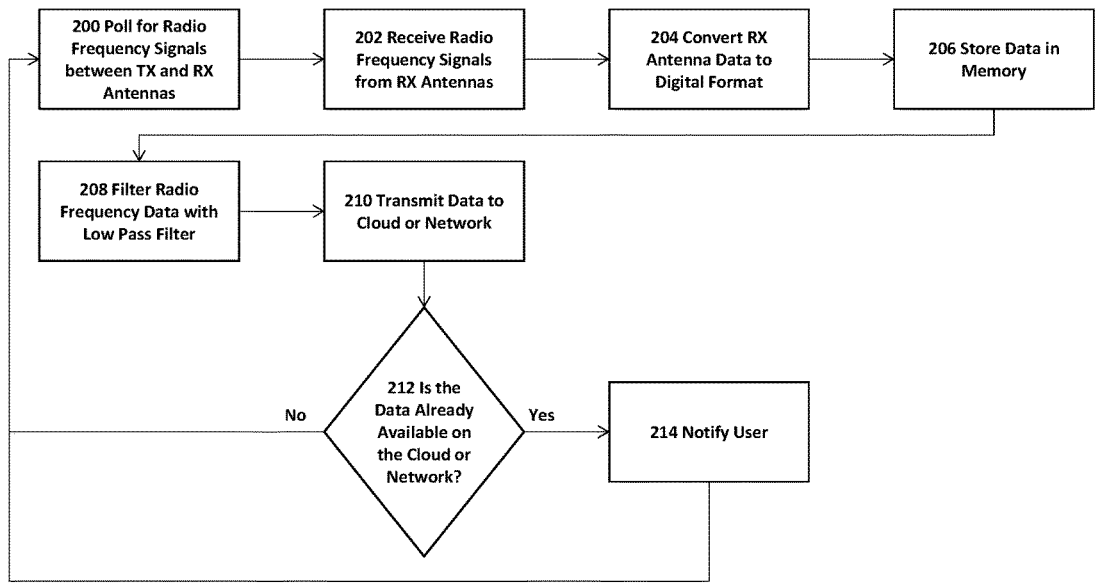

FIG. 2: Illustrates an example operation of the Device Base Module, according to an embodiment.

Figure 3:
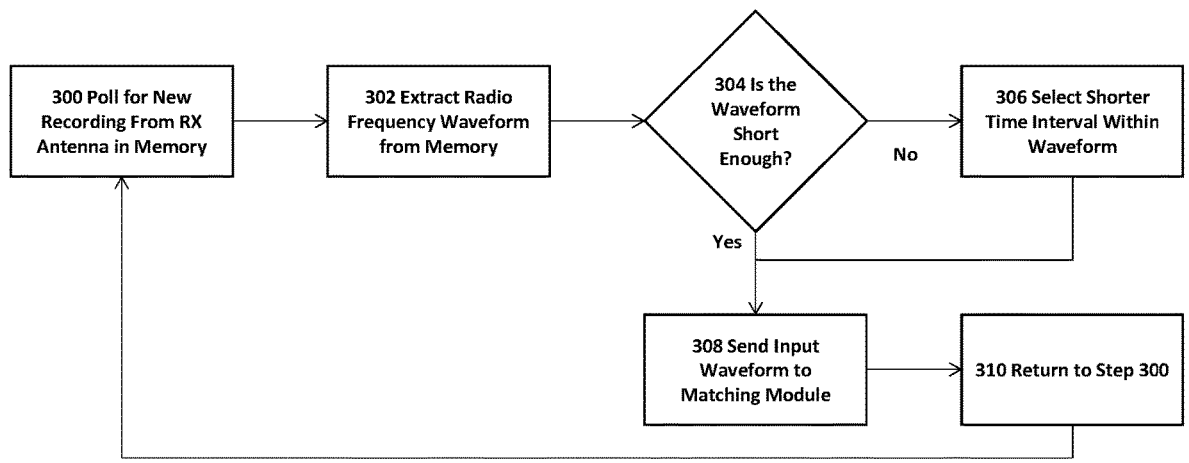

FIG. 3: Illustrates an example operation of the Input Waveform Module, according to an embodiment.

Figure 4:
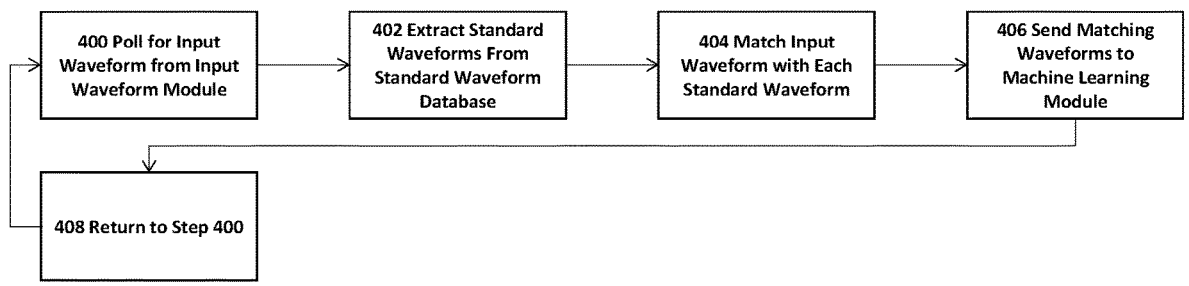

FIG. 4: Illustrates an example operation of the Matching Module, according to an embodiment.

Figure 5:
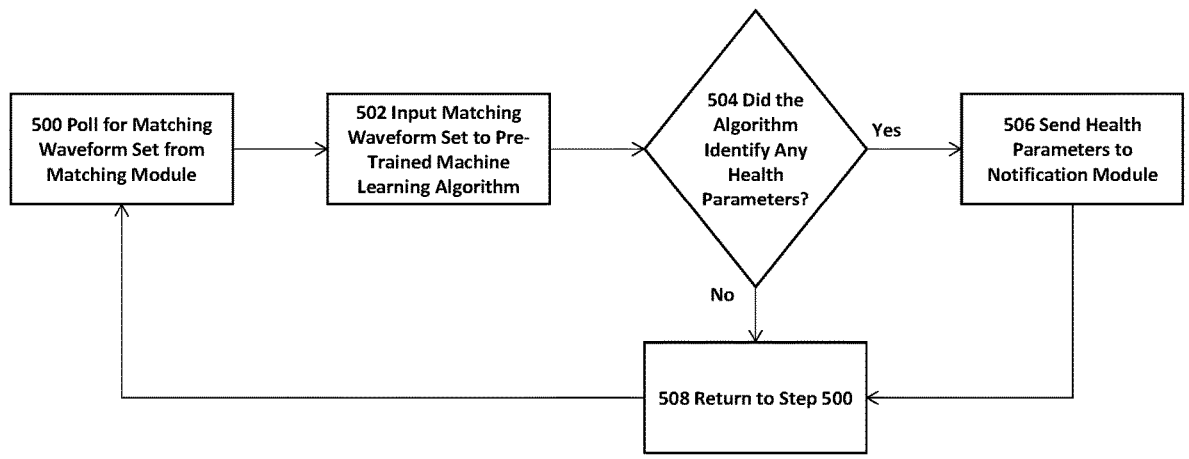

FIG. 5: Illustrates an example operation of the Machine Learning Module, according to an embodiment.

Figure 6:
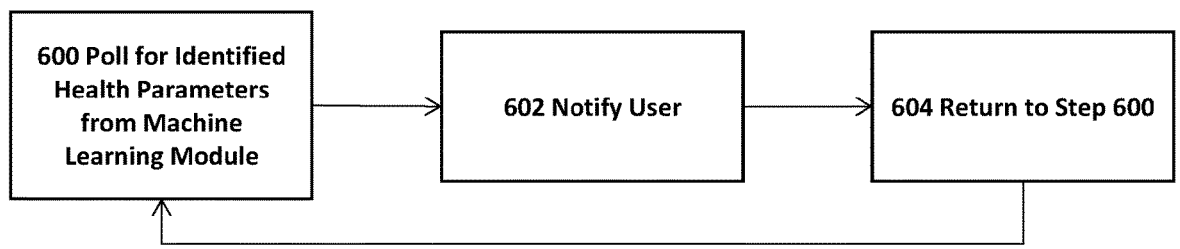

FIG. 6: Illustrates an example operation of the Notification Module, according to an embodiment.

Figure 7:
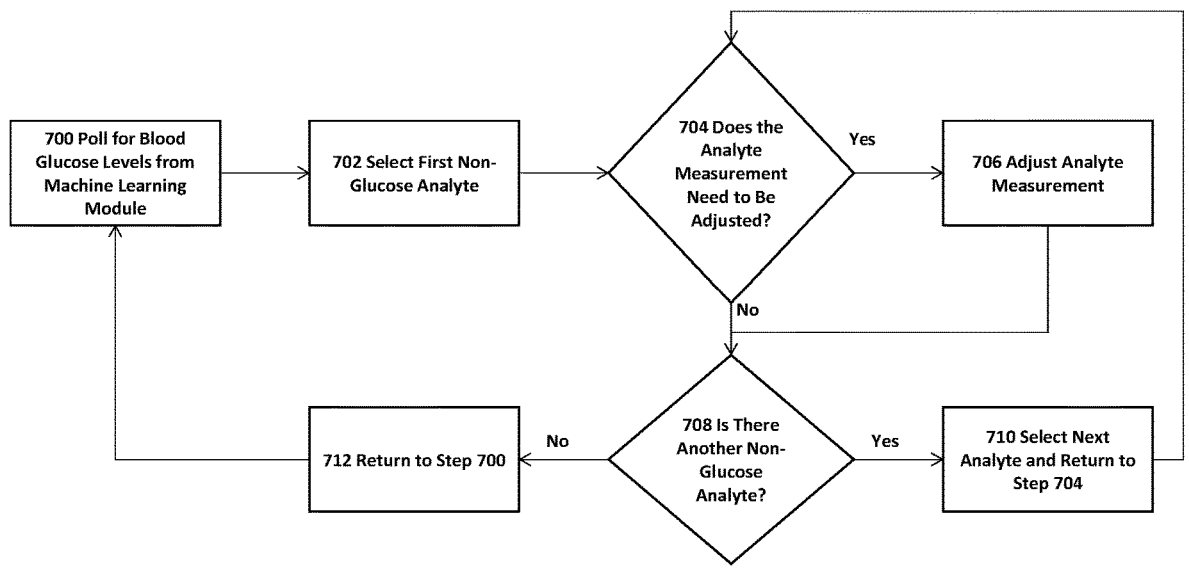

FIG. 7: Illustrates an example operation of the Analyte Adjust Module, according to an embodiment.

Figure 8:
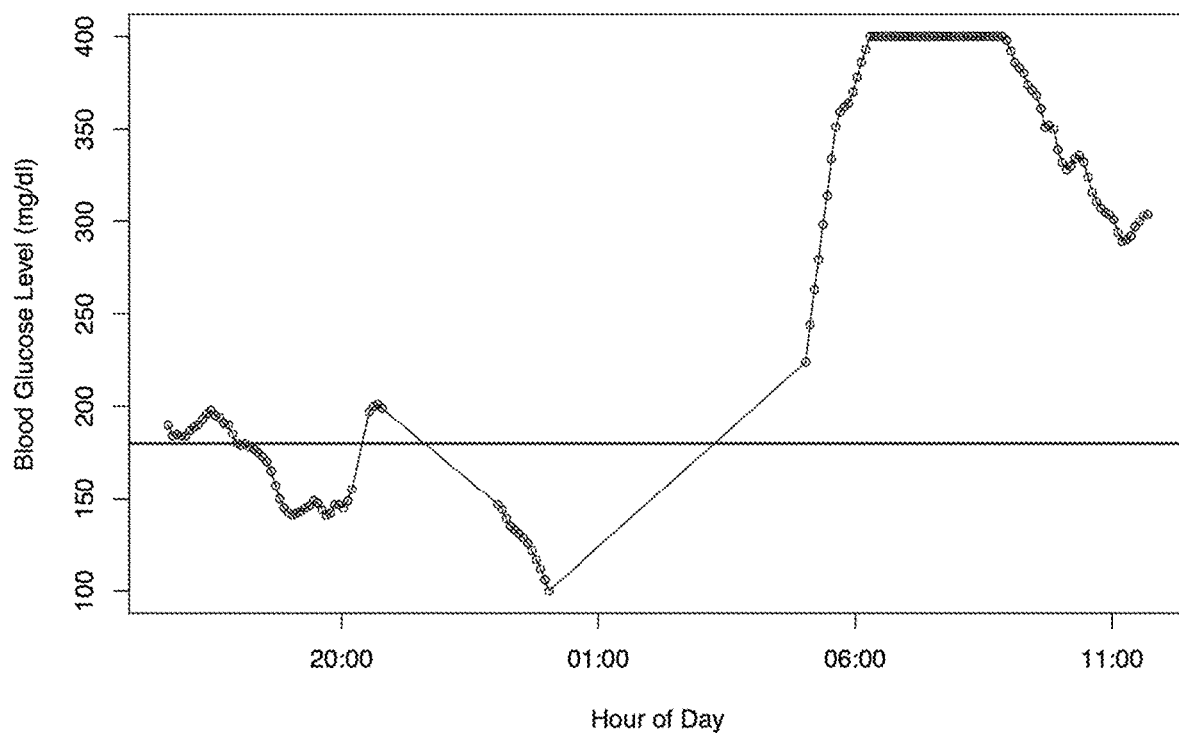

FIG. 8: Illustrates an example of a Glucose Waveform, according to an embodiment.

Figure 9:
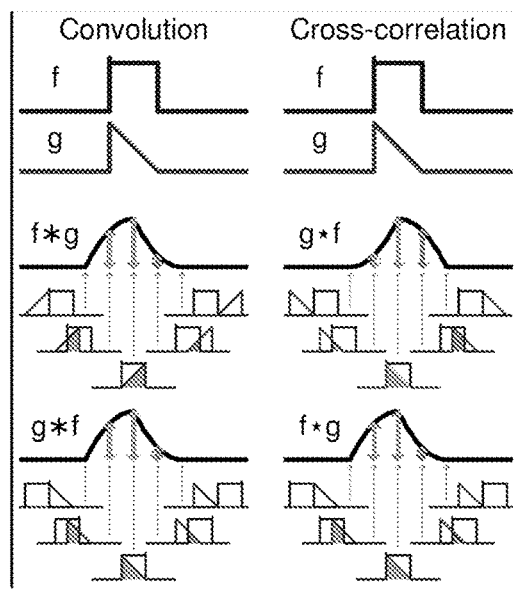

FIG. 9: Illustrates an example of Matching Methods, according to an embodiment.

Figure 10:
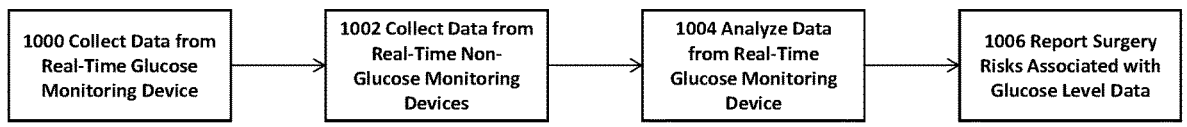

FIG. 10: Illustrates a method, according to an embodiment.

Figure 11:
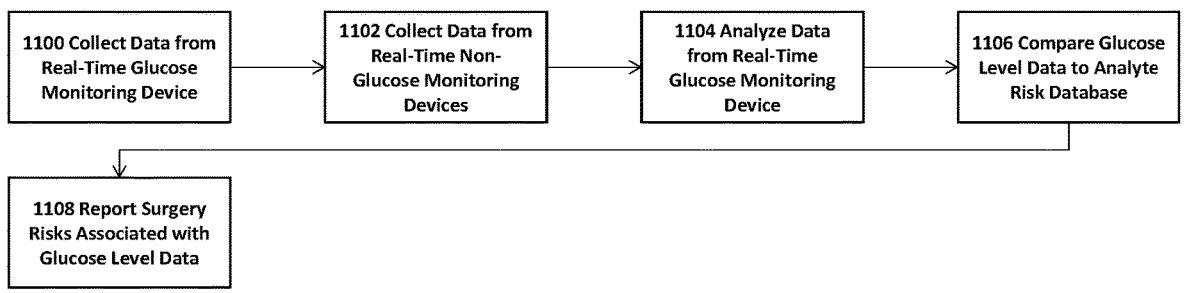

FIG. 11: Illustrates another method, according to an embodiment.

Figure 12:
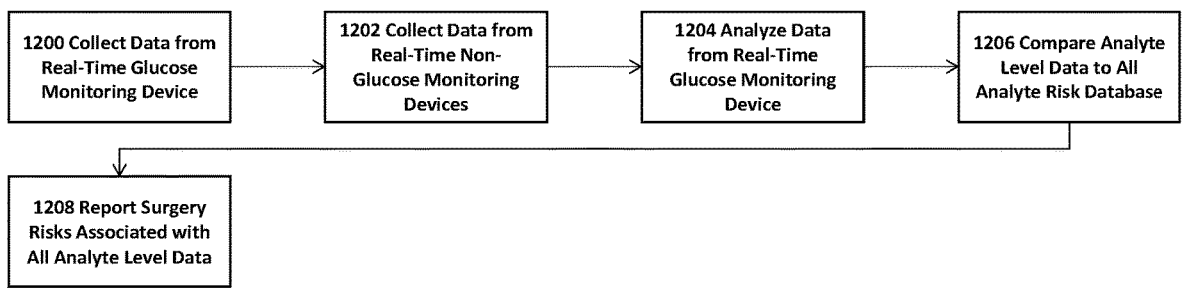

FIG. 12: Illustrates another method, according to an embodiment.

DETAILED DESCRIPTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

U.S. Pat. Nos. 10,548,503, 11,063,373, 11,058,331, 11,033,208, 11,284,819, 11,284,820, 10,548,503, 11,234,619, 11,031,970, 11,223,383, 11,058,317, 11,193,923, 11,234,618, 11,389,091, U.S. 2021/0259571, U.S. 2022/0077918, U.S. 2022/0071527, U.S. 2022/0074870, U.S. 2022/0151553, are each individually incorporated herein by reference in its entirety.

FIG. 1 displays a radio frequency health monitoring system. This system comprises a body part 102 to which the device 108 may be attached. The body part 102 may be an arm 104. The body part 102 may be the other arm of the patient or another body part 106 besides an arm, such as a leg, finger, chest, head, or any other body part from which useful medical parameters can be taken. The system may further comprise a device 108, which may be a wearable and portable device such as, but not limited to, a cell phone, a smartwatch, a tracker, a wearable monitor, a wristband, and a personal blood monitoring device. The system may further comprise a set of TX antennas 110 and RX antennas 156. TX antennas 110 may be configured to transmit RF signals in the RF Activated Range from 500 MHZ to 300 GHZ. In one embodiment, a pre-defined frequency may correspond to a range suitable for the human body. For example, the one or more TX antennas 110 can use radio frequency signals at a range of 120-126 GHz. Successively, the one or more RX antennas 156 may be configured to receive the RF signals in response to the TX RF signal. The system may further comprise an ADC converter 112, which may be configured to convert the RF signals received by the RX antenna 156 from an analog signal into a digital processor readable format. The system may further comprise memory 114, which may be configured to store the transmitted RF signals by the one or more TX antennas 110 and receive a portion of the received RF signals from the one or more RX antennas 156. Further, the memory 114 may also store the converted digital processor readable format by the ADC converter 112. The memory 114 may include suitable logic, circuitry, and/or interfaces that may be configured to store a machine code and/or a computer program with at least one code section executable by the processor 118. Examples of implementation of the memory 114 may include, but are not limited to, Random Access Memory (RAM), Read Only Memory (ROM), Hard Disk Drive (HDD), and/or a Secure Digital (SD) card.

The system may further comprise a standard waveform database 116, which may contain standard waveforms for known patterns. These may be raw or converted device readings from patients or persons with known conditions. For example, the standard waveform database 116 may include raw or converted device readings from the patient, for example the right arm, known to have diabetes or an average of multiple patients. This data can be compared to readings from a person with an unknown condition to determine if the waveforms from that person match any of the known standard waveforms.

The system may further comprise a processor 118, which may facilitate the operation of the device 108 according to the instructions stored in the memory 114. The processor 118 may include suitable logic, circuitry, interfaces, and/or code that may be configured to execute a set of instructions stored in the memory 114.

The system may further comprise comms 120, which may communicate with a network.

Examples of networks may include, but are not limited to, the Internet, a cloud network, a Wireless Fidelity (Wi-Fi) network, a Wireless Local Area Network (WLAN), a Local Area Network (LAN), a telephone line (POTS), Long Term Evolution (LTE), and/or a Metropolitan Area Network (MAN).

The system may further comprise a battery 122, which may power hardware modules of the device 108. The device 108 may be configured with a charging port to recharge the battery 122. Charging of the battery 122 may be achieved via wired or wireless means.

The system may further comprise a device base module 124, which may be configured to store instructions for executing the computer program on the converted digital processor readable format of the ADC converter 112. The device base module 124 may be configured to facilitate the operation of the processor 118, the memory 114, the TX antennas 110 and RX antennas 156, and the comms 120. Further, the device base module 124 may be configured to create polling of the RF Activated Range signals from 500 MHZ to 300 GHZ. It can be noted that the device base module 124 may be configured to filter the RF Activated Range signals from 500 MHZ to 300 GHZ received from one or more RX antennas 156.

The system may further comprise an input waveform module 126, which may extract a radio frequency waveform from memory. This may be the raw or converted data recording from the RX antennas 156 from a patient wearing the device. If the entire radio frequency is too long for effective matching, the input waveform module 126 may select a time interval within the data set. This input waveform may then be sent to the matching module 128.

The system may further comprise a matching module 128, which may match the input waveform and each of the standard waveforms in the standard waveform database 116 by performing a convolution and/or cross-correlation of the input waveform and the standard waveform. These convolutions and/or cross-correlations are then sent to the machine learning module 130.

The system may further comprise a machine learning module 130 which has been trained to identify health parameters based on the convolution and/or cross-correlations of the input and standard waveforms. The machine learning module 130 receives the convolutions and cross-correlations from the matching module 128 and outputs any health parameters identified. The system may further comprise a notification module 132, which may determine if any of the health parameters output by the machine learning module 130 require a notification. If so, the patient and/or the patient's medical care providers may be notified. The system may further comprise an analyte adjust module 134, which may adjust measurements of non-glucose analytes based on measured glucose levels. For example, SpO2 can get overestimated with high glucose levels, so if glucose measurements show a high glucose level, the SpO2 measurements may need to be adjusted downward.

In some embodiments, the device base module 124 may utilize a motion module 144 that includes at least one sensor from the group of an accelerometer, a gyroscope, an inertial movement sensor, or other similar sensor. There are some operations or surgeries where the patient may need to move during the procedure. These procedures are typically performed under local anesthesia, and the patient may be awake or lightly sedated.

One example is deep brain stimulation surgery, which is used to treat movement disorders such as Parkinson's disease. During this surgery, the patient is awake and may be asked to perform certain movements or tasks to help the surgeon identify the target area in the brain for the electrode implantation.

Another example is spinal surgery, where the patient may need to move or change positions during the procedure to allow the surgeon to access the affected area. In some cases, the patient may be asked to sit or stand to help the surgeon determine the proper placement of the surgical instruments.

Similarly, some orthopedic procedures may require the patient to move or perform certain movements during the surgery to assist the surgeon in adjusting or aligning the affected bone or joint.

The motion module 144 may have its own processor or utilize the processor 118 to calculate the user's movement. Motion from the user will change the blood volume in a given portion of their body and the blood flow rate in their circulatory system. This may cause noise, artifacts, or other errors in the real-time signals received by the RX antennas 156. The motion module 144 may compare the calculated motion to a motion threshold stored in memory 114. For example, the motion threshold could be movement of more than two centimeters in one second. The motion threshold could be near zero to ensure the user is stationary when measuring to ensure the least noise in the RF signal data. When calculated motion levels exceed the motion threshold, the motion module 144 may flag the RF signals collected at the time stamp corresponding to the motion as potentially inaccurate. In some embodiments, the motion module 144 may compare RF signal data to motion data over time to improve the accuracy of the motion threshold. The motion module 144 may alert the nurse, doctor, or medical staff, such as with an audible beep or warning or a text message or alert to a connected mobile device. The alert would signal the nurse, doctor, or medical staff that the patient is moving too much to get an accurate measurement. The motion module 144 may update the standard waveform database 116 with the calculated motion of the user that corresponds with the received RF signal data. In this manner, the motion module 144 may be simplified to just collect motion data and allow the device base module 124 to determine if the amount of motion calculated exceeds a threshold that would indicate the received RF signal data is too noisy to be relied upon for a blood glucose measurement.

The device base module 124 may utilize a body temperature module 146 that includes at least one sensor from the group of a thermometer, a platinum resistance thermometer (PRT), a thermistor, a thermocouple, or another temperature sensor. The body temperature module 146 may have its own processor or utilize the processor 118 to calculate the temperature of the user or the user's environment. The user's body temperature, the environmental temperature, and the difference between the two will change the blood volume in a given part of their body and the blood flow rate in their circulatory system. Variations in temperature from the normal body temperature or room temperature may cause noise, artifacts, or other errors in the real-time signals received by the RX antennas 156. The body temperature module 146 may compare the measured temperature to a threshold temperature stored in memory 114. For example, the environmental temperature threshold may be set at zero degrees Celsius because low temperatures can cause a temporary narrowing of blood vessels which may increase the user's blood pressure. When the measured temperature exceeds the threshold, the body temperature module 146 may flag the RF signals collected at the time stamp corresponding to the temperature as potentially being inaccurate. In some embodiments, the body temperature module 146 may compare RF signal data to temperature data over time to improve the accuracy of the temperature threshold. The body temperature module 146 may alert the nurse, doctor or medical staff, such as with an audible beep or warning or a text message or alert to a connected mobile device. The alert would signal to the nurse, doctor or medical staff that the patient's body temperature, or the environmental temperature is not conducive to getting an accurate measurement. The body temperature module 146 update the standard waveform database 116 with the measured user or environmental temperature that corresponds with the received RF signal data. In this manner, the body temperature module 146 may be simplified to just collect temperature data and allow the device base module 124 to determine if the temperature measure exceeds a threshold that would indicate the received RF signal data is too noisy to be relied upon for a blood glucose measurement.

The device base module 124 may utilize an ECG module 150 that includes at least one electrocardiogram sensor. The ECG module 150 may have its own processor or utilize the processor 118 to record the electrical signals that correspond with the user's heartbeat. The user's heartbeat will impact blood flow. Measuring the ECG data may allow the received RF data to be associated with peak and minimum cardiac output so as to create a pulse waveform allowing for the estimation of blood volume at a given point in the wave of ECG data. Variations in blood volume may cause noise, artifacts, or other errors in the real-time signals received by the RX antennas 156. The ECG module 150 may compare the measured cardiac data to a threshold stored in memory 114. For example, the threshold may be a pulse above 160 bpm, as the increased blood flow volume may cause too much noise in the received RF signal data to accurately measure the blood glucose. When the ECG data exceeds the threshold, the ECG module 150 may flag the RF signals collected at the time stamp corresponding to the ECG data as potentially being inaccurate. In some embodiments, the ECG module 150 may compare RF signal data to ECG data over time to improve the accuracy of the ECG data threshold or to improve the measurement of glucose at a given point in the cycle between peak and minimum cardiac output. The ECG module 150 may alert the nurse, doctor or medical staff, such as with an audible beep or warning or a text message or alert to a connected mobile device. The alert would signal to the nurse, doctor or medical staff that their heart rate is not conducive to getting an accurate measurement or requires additional medical intervention. The ECG module 150 may update the standard waveform database 116 with the measured ECG data that corresponds with the received RF signal data. In this manner, the ECG module 150 may be simplified to just collect ECG data and allow the device base module 124 to determine if the ECG data exceeded a threshold that would indicate the received RF signal data is too noisy to be relied upon for a blood glucose measurement.

The device base module 124 may include a received noise module 154 that includes at least one sensor measuring background signals such as RF signals, Wi-Fi, and other electromagnetic signals that could interfere with the signals received by the RX antennas 156. The received noise module 154 may have its own processor or utilize the processor 118 to calculate the level of background noise being received. Background noise may interfere with or cause noise, artifacts, or other errors or inaccuracies in the real-time signals received by the RX antennas 156. The received noise module 154 may compare the level and type of background noise to a threshold stored in memory 114. The threshold may be in terms of field strength (volts per meter and ampere per meter) or power density (watts per square meter). For example, the threshold may be RF radiation greater than 300 u W/m2. When the background noise data exceeds the threshold, the received noise module 154 may flag the RF signals collected at the time stamp corresponding to background noise levels as potentially being inaccurate. In some embodiments, the received noise module 154 may compare RF signal data to background noise over time to improve the accuracy of the noise thresholds. The received radiation module may alert the nurse, doctor or medical staff, such as with an audible beep or warning, a text message, or an alert to a connected mobile device. The alert would signal to the nurse, doctor or medical staff that the current level of background noise is not conducive to getting an accurate measurement. The received noise module 154 may update the standard waveform database 116 with the background noise data that corresponds with the received RF signal data. In this manner, the received noise module 154 may be simplified to just collect background noise data and allow the device base module 124 to determine if the measure exceeded a threshold that would indicate the received RF signal data is too noisy to be relied upon for a blood glucose measurement, or if an alternative transfer function should be used to compensate for the noise.

In embodiments, one or more of memory 114, standard waveform database 116, input waveform module 126, matching module 128, the machine learning module 130, the notification module 132, the analyte adjust module 134, the motion module 144, the body temperature module 146, the ECG module 150, and/or the received noise module 154 can be provided on one or more separate devices, such as cloud server 134, the networked device 136, or the like. In such embodiments, the comms 120 can be used to communicate with the cloud server 134 or the networked device 136 to access the memory 114, standard waveform database 116, input waveform module 126, matching module 128, the machine learning module 130, the notification module 132, the analyte adjust module 134, the motion module 144, the body temperature module 146, the ECG module 150, and/or the received noise module 154 by way of any suitable network.

The system may further comprise a third-party network 140, which may be a computer or network of computers controlled by a third-party such as a hospital, data collection service, medical record service, insurance company, university, etc. The system may further comprise an analyte risk database 142, which may contain risks associated with levels of glucose and other analytes in the blood during surgical procedures. Surgical procedures can include pre-operative preparation, the performance of the surgical operation itself, and post-operative activities such as suturing, recovery from anesthesia, disinfection of the patient, and the like. The system may further comprise one or more non-glucose measurement devices 156, which may be a sphygmomanometer, a pulse oximeter, an electrocardiogram, a holter monitor, a thermometer, or other patient monitoring device known in the art.

FIG. 2 illustrates an example operation of the device base module 124. The process may begin with the device base module 124 polling the Active Range RF signals between the one or more TX antennas 110 and the one or more RX antennas 156 at step 200. The device base module 124 may be configured to read and process instructions stored in the memory 114 using the processor 118. The TX antennas 110 may be configured to transmit RF signals in the RF Activated Range from 500 MHZ to 300 GHZ. For example, the one or more TX antennas 110 may transmit RF signals at a range of 500 MHZ to 300 GHZ. The device base module 124 may receive the RF frequency signals from the one or more RX antennas 156 at step 202. For example, an RX antenna receives an RF of frequency range 300-330 GHz from the patient's blood. The device base module 124 may be configured to convert the received RF signals into a digital format using the ADC 112 at step 204. For example, the received RF signals of frequency range 300-330 GHz is converted into a 10-bit data signal. The device base module 124 may be configured to store converted digital format into the memory 114 at step 206. The device base module 124 may be configured to filter the stored RF signals at step 208. The device base module 124 may be configured to filter each RF signal using a low pass filter. For example, the device base module 124 filters the RF signals of frequency range 300-330 GHz to RF signals of frequency range 300-310 GHz The device base module 124 may be configured to transmit the filtered RF signals to the cloud or other network using the comms module 120 at step 210. For example, the device base module 124 may be configured to transmit RF signals in the RF Activated Range from 500 MHZ to 300 GHZ to the cloud. The device base module 124 may be configured to determine whether the transmitted data is already available in the cloud or other network at step 212. The device base module 124, using the comms 120, communicates with the cloud network to determine that the transmitted RF signal is already available. The device base module 124 may determine that the transmitted data is not already present in the cloud. The device base module 124 may then be redirected back to step 200 to poll the RF signals between the one or more TX antennas 110 and the one or more RX antennas 156. For example, the device base module 124 determines that the transmitted RF signal in the RF Activated Range from 500 MHZ to 300 GHZ is not present in the cloud, and corresponding to the transmitted signal, there is no data related to the blood glucose level of the patient. The device base module 124 may determine that transmitted data is already present in the cloud. For example, the device base module 124 reads cloud notification of the patient's blood glucose level as 110 mg/dL corresponding to an RF signal in the RF Activated Range from 500 MHZ to 300 GHZ. The device base module 124 may continue to step 214. The device base module 124 may notify the nurse, doctor or medical staff via the device 108 of health information, for example, blood glucose level.

FIG. 3 illustrates an example operation of the input waveform module 126. The process may begin with the input waveform module 126 polling, at step 300, for newly recorded data from the RX antennas 156 stored in memory 114. The input waveform module 126 may extract, at step 302, the recorded radio frequency waveform from memory. If there is more than one waveform recorded, the input waveform module 126 may select each waveform separately and loop through the following steps. The input waveform module 126 may determine, at step 304, if the waveform is small enough to be an input waveform for the matching module 128. This will depend on the computational requirements and/or restrictions of the matching module 128. If the waveform is short enough, the input waveform module 126 may skip to step 308. If the waveform is too long, the input waveform module 126 may select, at step 306, a shorter time interval within the entire recorded waveform. For example, if the waveform is 5 minutes long, then only a 30-second interval may be selected. The interval may be selected at random or by a selection process. The input waveform module 126 may send, at step 308, the input waveform to the matching module 128. The input waveform module 126 may return, at step 310, to step 300.

FIG. 4 illustrates an example operation of the matching module 128. The process may begin with the matching module 128 polling, at step 400, for an input waveform from the input waveform module 126. The matching module 128 may extract, at step 402, each standard waveform from the standard waveform database 116. The matching module 128 may match, at step 404, the input waveform with each standard waveform. Matching may be determining which standard waveforms the input waveform is similar to. Matching may involve convolution and/or cross-correlation of the waveforms or any other suitable matching technique. Cross-correlation and convolution are mathematical operations that can be used to determine the similarity between two wave functions. They are often used in signal processing and image recognition applications to find patterns or features in data. Cross-correlation measures the similarity between two signals as a function of the time lag applied to one of them. It is defined as the integral of the product of two signals after one is flipped and delayed by some amount. By running the cross-correlation function on two wave functions, the output will give a similarity value between two signals, where the highest value represents the most similar pair. Convolution, on the other hand, is a mathematical operation that combines two functions to produce a third function. It is the integral of the product of two functions after one of them is flipped and then shifted. By applying convolution on two wave functions, the output will be a function in which values represent the degree of similarity between input signals, where higher values represent more similar signals. These operations may be used in combination with other techniques, such as the Fourier transform, to extract information from signals and compare them. Matching waveforms may be waveforms where the cross-correlation and/or convolution values are close to 1 with respect to time. For example, the threshold value may be 0.85. Any point in the function that results from cross-correlation above 0.85 may indicate that the standard waveform matches the input waveform. Matching standard waveforms, the input waveform, the cross-correlation of both, and/or the convolution of both may be used as an input to the machine learning algorithm of the machine learning module 130. The matching module 128 may send, at step 406, the matching waveforms to the machine learning module 130. Matching waveforms may refer to the standard waveforms that were similar to the input waveform, the waveforms that were generated via convolution and/or cross-correlation, or both. The matching module 128 may return, at step 408, to step 400.

FIG. 5 illustrates an example operation of the machine learning module 130. The process may begin with the machine learning module 130 polling, at step 500, for a set of matching waveforms from the matching module 128. Matching waveforms may be a set of standard waveforms similar to the input waveform or statistical combinations of the input waveform and standard waveforms, such as convolutions or cross-correlations. The machine learning module 130 may input, at step 502, the set of received waveforms into a pre-trained machine learning algorithm. The machine learning algorithm may be trained on similar sets of matched waveforms where the input waveform is from a patient whose health parameters are known. The waveforms may be input directly into the algorithm, such as a set of X and Y values. The matching waveforms may each be summarized as a closest fit function or may be transformed into a set of sine waves using a Fourier transform. Training data should be labeled with the correct output, such as the type of waveform. In order to prepare the data, the waveforms need to be processed and converted into a format that can be used by the algorithm. Once the data is prepared, the algorithm is trained on the labeled data. The model uses this data to learn the relationships between the waveforms and their corresponding outputs. During training, the model will adjust its parameters to minimize errors between its predictions and the correct outputs. Once the model has been trained and fine-tuned, it can be used to recognize waveforms in new, unseen data. This could be done by giving the input waveforms, then the algorithm will predict the health parameters. The machine learning module 130 may determine, at step 504, if the algorithm identified any health parameters. Identification may require a certain interval of confidence. For example, if the machine learning algorithm determines that it is more than 70% likely that a health parameter is correct, then that parameter may be considered identified. If multiple conflicting parameters exist, then the most confident may be used. For example, if the algorithm determines that it is 75% likely that the patient's blood glucose level is between 110-115 mg/dL and 90% likely that the patient's blood glucose is between 105-110 mg/dL, then the more confident value of 105-110 mg/dL may be identified. If none of the results from the machine learning algorithm are above the confidence threshold, or the results are otherwise inconclusive, the machine learning module 130 may skip to step 508. If any health parameters were identified, the machine learning module 130 may send, at step 506, the health parameters to the notification module 132. The machine learning module 130 may return, at step 508, to step 500.

FIG. 6 illustrates an example operation of the notification module 132. The process may begin with the notification module 132 polling, at step 600, for health parameters identified by the machine learning module 130. The notification module 132 may notify, at step 602, the nurse, doctor or medical staff of the device and/or their care providers. For example, the device may display a readable interface with the identified health parameters such as heart rate, blood pressure, blood glucose, oxygen level, etc. This information may be sent via the comms 120 to another device, such as a terminal in a nursing station, doctor's office, emergency medical transport office, etc. Notification may include audio or haptic feedback such as beeping or vibrating. The notification module 132 may return, at step 604, to step 600.

FIG. 7 illustrates an example operation of the analyte adjust module 134. The process may begin with the analyte adjust module 134 polling, at step 700, for blood glucose levels determined by the machine learning module 130. The analyte adjust module 134 may select, at step 702, the first non-glucose analyte for which there is incoming data. For example, SpO2, carbon dioxide, hemoglobin, sodium, potassium, etc. The analyte adjust module 134 may determine, at step 704, if the analyte measurement needs to be adjusted. This determination may be made by checking a database of known adjustments based on glucose levels. For example, studies have found that SpO2 can be overestimated when blood glucose is high. Therefore, the SpO2 level may be adjusted downward by 1% for every 5 mg/dL above average glucose levels based on a formula stored in a database which may be supported by medical literature. Alternatively, the adjustments may be learned by the system using a machine learning algorithm. If the selected analyte is unaffected by glucose level, or the current glucose level is not within a range that may affect the selected analyte, the analyte adjust module 134 may skip to step 708. If the measurement of the selected analyte needs to be adjusted, the analyte adjust module 134 may adjust, at step 706, the measurement. For example, SpO2 is measured at 96%, and glucose is 120 mg/dL. Based on a known formula for each 5 mg/dL above 100 mg/dL of blood glucose, SpO2 should be adjusted down by 1%. The measured SpO2 level would be adjusted down 4% to 92%. This adjustment may be applied to incoming SpO2 measurements and/or recently recorded SpO2 measurements. For another example, BAC is recorded at 0.06%, and glucose is 80 mg/dL. Based on a known set of rules, such as when glucose is <81 mg/dL, the BAC measurement is adjusted to an indeterminate value, indicating the test is inconclusive because low blood sugar can cause false positives on BAC tests. The analyte adjust module 134 may also, or instead, warn medical staff that an adjustment may need to be made and/or that the current reading for the selected analyte may be inaccurate. The analyte adjust module 134 may determine, at step 708, if another non-glucose analyte has not been selected. If there is another non-glucose analyte, the analyte adjust module 134 may select, at step 710, the next analyte and return to step 704. If there are no other non-glucose analytes, the analyte adjust module 134 may return, at step 712, to step 700.

FIG. 8 displays an example of a glucose waveform. The figure shows blood glucose levels in a patient recorded over time. A computer can store a waveform by digitizing the analog signal and storing the resulting digital values in memory. Digitization is typically accomplished by an analog-to-digital converter (ADC), which samples the amplitude of the analog signal at regular intervals and converts each sample to a digital value. The resulting digital values and information about the sampling rate and bit depth can be used to reconstruct the original waveform when the data is played back. The digital values could be stored in an array or binary files. The computer may store the important parts of the waveform, such as local and/or absolute maxima and minima, inflection points, inversion points, average value, best-fit line or function, etc.

FIG. 9 displays an example of matching methods such as convolution and cross-correlation. The figure illustrates two different matching methods, convolution, and cross-correlation. In the convolution process, the standard waveform slides over the input waveform, element-wise multiplying and summing the overlapping values. The result is a new output waveform. The convolution operation is useful for detecting specific features, such as edges, in the input waveform. In the cross-correlation process, the standard waveform is also sliding over the input waveform, element-wise multiplying and summing the overlapping values. However, the output waveform is not generated by summing the product of the standard waveform and the overlapping part of the input waveform but by taking the dot product of the standard waveform and the input waveform. The cross-correlation operation is used to find patterns in the input waveform that are similar to the standard waveform. Convolution and cross-correlation are similar operations used for waveform processing and pattern recognition. They are widely used in image processing, machine learning, computer vision, and waveform processing applications. This is a general description; these methods' actual implementation will depend on the specific use case and application.

FIG. 10 illustrates an example of a method that may be performed manually and/or automatically by the processor 118. The process may begin with collecting, at step 1000, data from a device 108 that provides real-time monitoring of glucose levels in a patient's blood. The process may continue with collecting, at step 1002, data from one or more devices 108 that provide real-time monitoring of non-glucose analytes in the patient's blood, such as oxygen, carbon dioxide, hemoglobin, sodium, potassium, or any analyte. The collection in step 1002 can be performed using any suitable monitoring device(s) including, but not limited to, those which may detect non-glucose analytes using radio frequency signal analysis. The process may continue with analyzing, at step 1004, the data collected from the real-time glucose monitoring device 108. Analysis of the data may involve converting raw data into readable glucose level data using the input waveform module 126, matching module 128, and a machine learning module 130. Data from the non-glucose devices 108 may be used in this analysis to give context or remove noise. For example, data from a heart monitor may be used to remove artifacts from the raw data that corresponds to the patient's pulse, as the blood movement during heart contraction could cause a change in the interaction of the RF signals with the blood. For another example, data from a pulse oximeter may be used to adjust the glucose level because the glucose monitoring device 108 may be calibrated for blood with a specific SpO2, and an increase or decrease in SpO2 can cause the perceived glucose level to change. The process may continue with reporting, at step 1006, risks of surgical complications that may be caused by the patient's glucose levels. Surgical risks may include delayed healing, increased wound infection, kidney issues, heart and/or lung problems, neurological complications, stroke, etc.

FIG. 11 illustrates another example of a method that may be performed manually and/or automatically by the processor 118. The process may begin with collecting, at step 1100, data from a device 108 that provides real-time monitoring of glucose levels in a patient's blood. The process may continue with collecting, at step 1102, data from one or more devices 108 that provide real-time monitoring of non-glucose analytes in the patient's blood, such as oxygen, carbon dioxide, hemoglobin, sodium, potassium, or any analyte. The collection in step 1102 can be performed using any suitable monitoring device(s) including, but not limited to, those which may detect non-glucose analytes using radio frequency signal analysis. The process may continue with analyzing, at step 1104, the data collected from the real-time glucose monitoring device 108. Analysis of the data may involve converting raw data into readable glucose level data using the input waveform module 126, matching module 128, and a machine learning module 130. Data from the non-glucose devices 108 may be used in this analysis to give context or remove noise. For example, data from a heart monitor may be used to remove artifacts from the raw data that corresponds to the patient's pulse, as the blood movement during heart contraction could cause a change in the interaction of the RF signals with the blood. For another example, data from a pulse oximeter may be used to adjust the glucose level because the glucose monitoring device 108 may be calibrated for blood with a specific SpO2, and an increase or decrease in SpO2 can cause the perceived glucose level to change. The process may continue with comparing, at step 1106, the glucose level data from the device 108 to glucose level data in the analyte risk database 142, which may contain risks associated with levels of glucose and other analytes in the blood during surgical procedures. Surgical risks may include delayed healing, increased wound infection, kidney issues, heart and/or lung problems, neurological complications, stroke, etc. The process may continue with reporting, at step 1108, risks of surgical complications that may be caused by the patient's glucose levels based on the data in the analyte risk database 142.

FIG. 12 illustrates another example method that may be performed manually and/or automatically by the processor 118. The process may begin with collecting, at step 1200, data from a device 108 that provides real-time monitoring of glucose levels in a patient's blood. The process may continue with collecting, at step 1202, data from one or more devices 108 that provide real-time monitoring of non-glucose analytes in the patient's blood, such as oxygen, carbon dioxide, hemoglobin, sodium, potassium, or any analyte. The collection in step 1202 can be performed using any suitable monitoring device(s) including, but not limited to, those which may detect non-glucose analytes using radio frequency signal analysis. The process may continue with analyzing, at step 1204, the data collected from the real-time glucose monitoring device 108. Analysis of the data may involve converting raw data into readable glucose level data using the input waveform module 126, matching module 128, and a machine learning module 130. Data from the non-glucose devices 108 be used in this analysis to give context or remove noise. For example, data from a heart monitor may be used to remove artifacts from the raw data that corresponds to the patient's pulse, as the blood movement during heart contraction could cause a change in the interaction of the RF signals with the blood. For another example, data from a pulse oximeter may be used to adjust the glucose level because the glucose monitoring device 108 may be calibrated for blood with a specific SpO2, and an increase or decrease in SpO2 can cause the perceived glucose level to change. The process may continue by comparing, at step 1206, all analyte level data from the device 108 to analyte level data in the analyte risk database 142, which may contain risks associated with levels of glucose and other analytes in the blood during surgical procedures. Surgical risks may include delayed healing, increased wound infection, kidney issues, heart and/or lung problems, neurological complications, stroke, etc. Examples of blood analytes other than glucose may include hemoglobin, white blood cell count, cholesterol, creatinine, sodium, potassium, liver enzymes (AST, ALT), C-reactive protein (CRP), albumin, bilirubin, blood urea nitrogen (BUN), iron, lipase, magnesium, phosphorus, protein, and triglycerides. The process may continue with reporting, at step 1208, risks of surgical complications that may be caused by the patient's analyte levels based on the data in the analyte risk database 142.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

What is claimed is:

1. A method for performing surgery, comprising:
   during a surgical procedure on a patient, non-invasively measuring a glucose level in the patient, wherein non-invasively measuring the glucose level in the patient includes:
   transmitting, using one or more transmit antennas located within a glucose monitoring device, a transmit signal into a body of the patient during the surgical procedure, wherein the transmit signal is a radio frequency signal;
   receiving a modified radio frequency signal from the body of the patient using one or more receive antennas located within the glucose monitoring device, the modified radio frequency signal being responsive to the transmit signal; and
   at least one of:
   a) obtaining a movement of the patient using a motion module located within the glucose monitoring device, the motion module including an accelerometer, a gyroscope, or an inertial movement sensor;

comparing the movement of the patient to a motion threshold stored within a memory of the glucose monitoring device; and when the movement of the patient exceeds the motion threshold, flagging the modified radio frequency signal as potentially inaccurate; or b) obtaining a body temperature of the patient using a temperature module located within the glucose monitoring device, the temperature module including at least one of a thermometer, a thermistor, or a thermocouple;

comparing the body temperature of the patient to a temperature threshold stored within the memory of the glucose monitoring device; and when the body temperature of the patient exceeds the temperature threshold, flagging the modified radio frequency signal as potentially inaccurate;

based on the modified radio frequency signal not being flagged as potentially inaccurate, processing the modified radio frequency signal to determine the glucose level in the patient;

converting, using an analog-to-digital converter, the modified radio frequency signal to one or more digital response signals;

measuring, using a non-glucose analyte measurement device that is separate from the glucose monitoring device, a non-glucose analyte measurement and adjusting, using an analyte adjust module, the non-glucose analyte measurement based on the glucose level in the patient;

determining, using a processor, a complication risk of the surgical procedure based on the glucose level; and displaying the complication risk of the surgical procedure.

2. The method of claim 1, wherein processing the modified radio frequency signal to determine the glucose level includes matching the modified radio frequency signal to one or more waveforms of a waveform database and applying a machine learning algorithm to the matched modified radio frequency signal and waveforms.

3. The method of claim 1, wherein non-invasively measuring the glucose level is performed continuously during an entire duration of the surgical procedure.

4. The method of claim 1, wherein the complication risk includes a risk of one or more of: wound infection, kidney complications, heart complications, lung complications, neurological complications, and/or stroke.

5. The method of claim 1, wherein processing the modified radio frequency signal to determine the glucose level of the patient includes removing noise based on a pulse of the patient.

6. The method of claim 1, wherein processing the modified radio frequency signal to determine the glucose level of the patient includes removing noise based on a blood oxygenation of the patient.

7. The method of claim 1, wherein the measuring of the glucose level is performed in real-time.

8. A surgical care system, comprising:

a non-invasive radio frequency glucose monitoring device that is configured to non-invasively obtain real-time glucose readings from a patient using radio frequency signals during a surgical procedure on the patient, the non-invasive radio frequency glucose monitoring device including:

one or more transmit antennas located within the glucose monitoring device, the one or more transmit antennas configured to transmit radio frequency signals into a body of the patient during the surgical procedure; and one or more receive antennas located within the glucose monitoring device, the one or more receive antennas configured to obtain modified radio frequency signals returning from the body of the patient as a result of the radio frequency signals transmitted into the body of the patient and modified by the body of the patient during the surgical procedure, at least one of:

a) a motion module located within the glucose monitoring device, the motion module including an accelerometer, a gyroscope, or an inertial movement sensor, the motion module configured to:

obtain a movement of the patient;

compare the movement of the patient to a motion threshold stored within a memory of the glucose monitoring device; and when the movement of the patient exceeds the motion threshold, flag the modified radio frequency signals as potentially inaccurate; or b) a temperature module located within the glucose monitoring device, the temperature module including at least one of a thermometer, a thermistor, or a thermocouple, the temperature module configured to:

obtain a body temperature of the patient;

compare the body temperature of the patient to a temperature threshold stored within the memory of the glucose monitoring device; and when the body temperature of the patient exceeds the temperature threshold, flag the modified radio frequency signals as potentially inaccurate;

wherein, when the modified radio frequency signals are not flagged as potentially inaccurate, the non-invasive radio frequency glucose monitoring device is configured to determine the real-time glucose readings based on said modified radio frequency signals;

an analog-to-digital converter configured to convert the modified radio frequency signals to one or more digital response signals;

a non-glucose analyte measurement device that is separate from the glucose monitoring device, the non-glucose analyte measurement device including an analyte adjust module configured to obtain a non-glucose analyte measurement and adjust the non-glucose analyte measurement based on the real-time glucose readings;

a processor, configured to:

receive the real-time glucose readings from the non-invasive radio frequency glucose monitoring device; and determine a complication risk of the surgical procedure based on the real-time glucose readings; and a display configured to display the complication risk of the surgical procedure.

9. The surgical care system of claim 8, further comprising a waveform database that stores a plurality of waveforms, wherein the processor is configured to determine a glucose level by matching the modified radio frequency signals to one or more waveforms of the waveform database and applying a machine learning algorithm to the matched modified radio frequency signals and waveforms.

10. The method of claim 1, wherein the method includes obtaining the movement of the patient using the motion module located within the glucose monitoring device, the motion module including the accelerometer, the gyroscope, or the inertial movement sensor;

comparing the movement of the patient to the motion threshold stored within the memory of the glucose monitoring device; and when the movement of the patient exceeds the motion threshold, flagging the modified radio frequency signal as potentially inaccurate.

11. The method of claim 1, wherein the method includes obtaining the body temperature of the patient using the temperature module located within the glucose monitoring device, the temperature module including at least one of the thermometer, the thermistor, or the thermocouple;

comparing the body temperature of the patient to the temperature threshold stored within the memory of the glucose monitoring device; and when the body temperature of the patient exceeds the temperature threshold, flagging the modified radio frequency signal as potentially inaccurate.

12. The method of claim 1, wherein the method includes each of:

a) obtaining the movement of the patient using the motion module located within the glucose monitoring device, the motion module including the accelerometer, the gyroscope, or the inertial movement sensor;

comparing the movement of the patient to the motion threshold stored within the memory of the glucose monitoring device; and when the movement of the patient exceeds the motion threshold, flagging the modified radio frequency signal as potentially inaccurate; and b) obtaining the body temperature of the patient using the temperature module located within the glucose monitoring device, the temperature module including at least one of the thermometer, the thermistor, or the thermocouple;

comparing the body temperature of the patient to the temperature threshold stored within the memory of the glucose monitoring device; and when the body temperature of the patient exceeds the temperature threshold, flagging the modified radio frequency signal as potentially inaccurate.

13. The surgical care system of claim 8, wherein the surgical care system includes the motion module.

14. The surgical care system of claim 8, wherein the surgical care system includes the temperature module.

15. The surgical care system of claim 8, wherein the surgical care system includes each of the motion module and the temperature module.

* * * * *